United States Patent [19]

Dam et al.

[11] 4,166,961
[45] Sep. 4, 1979

[54] METHOD AND APPARATUS FOR DETECTING A BLOOD LEAK IN A HEMODIALYSIS SYSTEM

[75] Inventors: Naim G. Dam, New York; John P. Hufnagel, Mamaroneck, both of N.Y.

[73] Assignee: Hoechst Aktiengesellschaft, Franfurt am Main, Fed. Rep. of Germany

[21] Appl. No.: 888,859

[22] Filed: Mar. 22, 1978

[51] Int. Cl.² .................................... G01N 21/26
[52] U.S. Cl. ............................ 250/573; 250/574; 356/39
[58] Field of Search ............... 210/22 A, 22 C, 321; 250/573, 574, 575, 214 R; 356/39

[56] References Cited

U.S. PATENT DOCUMENTS

| 3,352,779 | 11/1967 | Austin et al. | 210/23 |
| 3,809,241 | 5/1974 | Alvine | 210/321 |
| 4,038,982 | 8/1977 | Burke et al. | 250/573 |

*Primary Examiner*—David C. Nelms
*Attorney, Agent, or Firm*—Curtis, Morris & Safford

[57] ABSTRACT

A blood leak in the dialyzer is detected by transmitting a pulsed beam of light into the dialysate flowstream at a predetermined angle of incidence between the central axis of the flowstream and the normal axis and measuring variations in reflecting light received by a photodetector arranged on the same side of the flowstream as the phototransmitter at a predetermined angle of reflection. The beam of light is interupted at a rate with a substantially equal on-time to off time ratio.

10 Claims, 4 Drawing Figures

METHOD AND APPARATUS FOR DETECTING A BLOOD LEAK IN A HEMODIALYSIS SYSTEM

This invention relates to a sensor system and method for detecting a blood leak in a hemodialysis system.

In the practice of artificial kidney dialysis, blood is withdrawn from the artery of the patient, circulated in an extracorporeal blood circuit through a dialyzer where it is detoxified artificially by dialysis and then returned to the patient. The dialysis operation involves the molecular transfer of waste substances from the blood to a dialysate solution by mechanical diffusion through a colloidal semi-permeable dialyzer member. The dialysate solution is circulated in an independent dialysate circuit separated from the extracorporeal blood circuit within the dialyzer by the semipermeable dialyzer member. The two liquid streams flow through the dialyzer in parallel. The dialyzer member is of any conventional type, such as, for example, a mass transfer elastomeric membrane of several millimeters in thickness or a hollow fiber bundle. The waste substances are preferably transferred through the dialyzer member with the assistance of a negative pressure gradient. The pores of the dialyzer member are too small to pass blood but are of sufficient size to pass waste. If a leak develops in the dialyzer member, the blood plasma will migrate into the dialysate circuit presenting a serious threat to the patient, particularly when the dialysis system operates in the preferred mode with a pressure differential across the dialyzer member. In the latter case, large quantities of blood are drawn through the dialyzer member into the dialysate solution. Because of the length of time required for dialysis, generally about six hours, and the inability of the patient to effectively guard against this hazard an automatic blood leak detection system is essential to a hemodialysis system.

Systems currently available for detecting blood leaks through a dialyzer member are based upon detecting variations in color in the dialysate solution. These systems operate by sensing differences in light transmission through the dialysate solution as a result of the variation in absorption properties between the dialysate solution constituents and blood plasma. In order to satisfactorily differentiate between variations in the absorption characteristics of the dialyzer solution and blood with any reasonable degree of sensitivity requires a relatively complex detection system which is inherently expensive.

It has been discovered in accordance with the present invention that by appropriate photoelectric alignment of a phototransmitter and photodetector a highly selective response to a blood leak through the dialyzer member is made possible by intermittently passing a beam of light into the dialysate solution and measuring variations in reflected light intensity. The method comprises the steps of: transmitting a narrow beam of light into said dialysate flowstream from one side thereof in a direction incident upon the central axis of the flowstream with a predetermined angle of incidence relative to an axis normal to said central axis; locating an optical receiver in a substantially common plane with said narrow beam of light and on the same side of said flowstream such that it forms an included angle of reflection with said normal axis substantially equal to said angle of incidence; interrupting said transmission of light at a relatively low repetition rate with the ratio of on time to off time being substantially equal; detecting the average DC level of the signal received by said optical receiver; and generating an alarm signal when said average DC level exceeds a predetermined level.

A further feature of the present invention resides in the use of a floating reference which avoids the need to recalibrate the system before dialyzing. In the past, recalibration was necessary because of variations in response due to thermal drift and from physical changes in the properties of constituents in the dialysate. The floating reference is established by a microprocessor which compares this signal against the detected optical signal to determine if an alarm should be sounded.

Accordingly, it is an object of the present invention to provide a method and system for detecting a blood leak in the dialysate flowstream of a hemodialysis system which is reliable, compact and inexpensive.

It is a further object of the present invention to provide a method and system which will detect the presence of blood in a dialysate flowstream with a minimum of calibration.

Further objects and advantages of the present invention will become apparent from the detailed description of the present invention when read in conjunction with the accompanying drawings of which:

The detector system of the present invention may be used with any conventional hemodialysis system. A preferred hemodialysis system in which the blood leak detector system of the present invention is particularly suited is shown and described in corresponding patent application Ser. No. 888,858 entitled Peristaltic Dialysate solution pump and Ser. No. 888,861 entitled Dearation Apparatus for Hemodialysis filed of this date herewith in the name of S. R. Savitz et al. The blood leak detector would be preferably mounted in the dialysate manifold for monitoring the dialysate after it has passed through the dialyzer cartridge and before it is either returned to the batch tank or discarded to waste.

Figure 1:
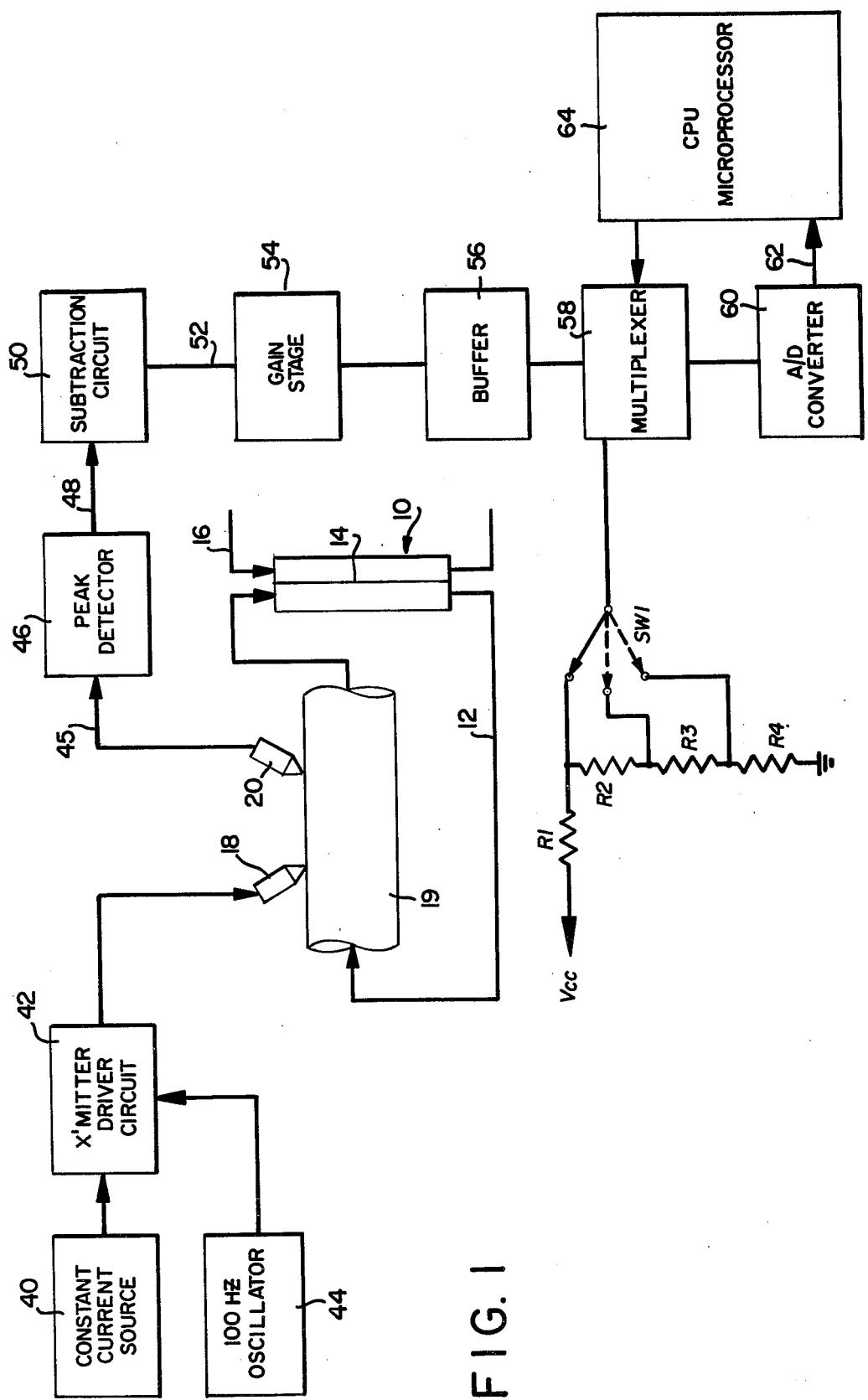
FIG. 1 is a schematic block diagram of the sensor system of the present invention.

Referring now to the drawings and in particular to FIG. 1 which diagrammatically illustrates a dialyzer 10 of any conventional geometry and construction defining two parallel paths separated by a dialyzer member 14. A dialysate solution circulates in a dialysate flow path 12 passing through the dialyzer 10 on one side of the dialyzer member 14. Blood plasma flows through an extracorporeal bloodcircuit 16 which passes through the dialyzer 10 on the opposite side of the dialyzer member 14.

Figure 2:
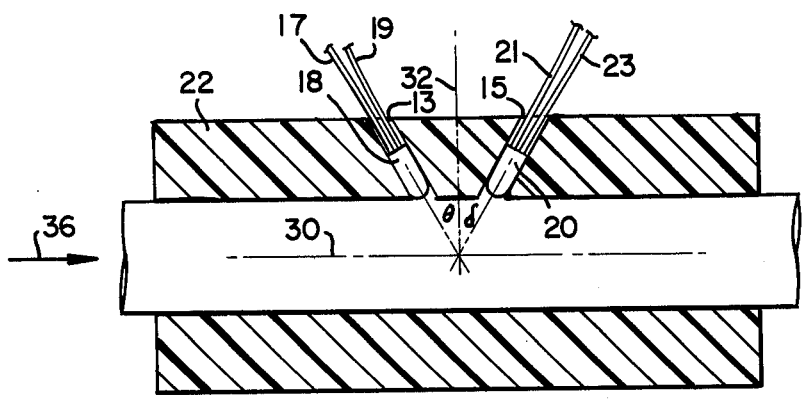
FIG. 2 is a cross-sectional view of the preferred optical transducer assembly for use in the system of FIG. 1.
Figure 3:
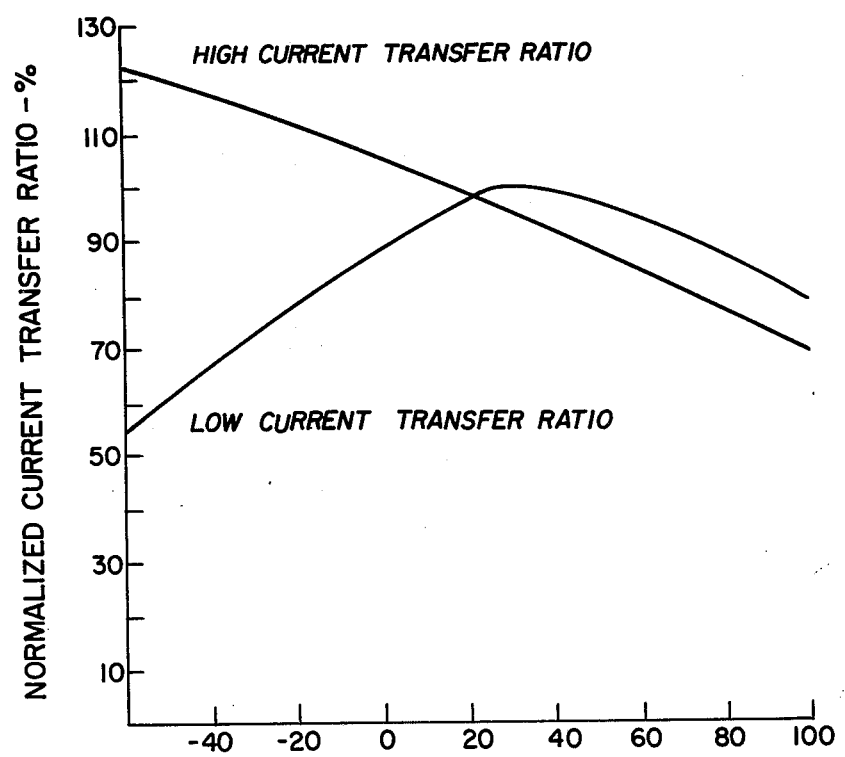
FIG. 3 is a graph of a typical current transfer ratio vs. temperature characteristic for a conventional solid state light emitting transducer.

An optical transmitter 18 and an optical receiver 20 are arranged for transmitting and receiving light through a section of tubing 19 of the dialysate circuit 12 which is preferably located downstream of the dialyzer 10. Reflected light through the dialysate is used to detect the presence of blood in the dialysate solution. The optical transmitter 18 and optical receiver 20 are assembled, as more clearly shown in FIG. 2, in a block 22, preferably of a plastic composition, such as acrylonitrile butadiene styrene, having a cylindrical bore adapted for mounting the block 22 about the section of tubing 19 of the dialysate flow path 12. The optical transmitter 18 and optical receiver 20 are inserted into drilled openings 13 and 15 formed in the block 22 so as to establish a predetermined orientation between the transducer elements 18 and 20 and the dialysate flowstream 26. Electrical leads 17, 11, 21 and 23 extend from the block 22 permitting the light transducer elements 18 and 20 to be secured within the drilled openings 13 and 15 by means of, for example, a conventional epoxy.

The optical transmitter 18 and optical receiver 20 are preferably aligned in the same plane on a common side relative to the dialysate flowstream 26. The transmitter 18 is directed at the central axis 30 of the flowstream 26 for forming a predetermined angle of incidence $\theta$ with respect to the normal axis 32. The receiver 20 should be located relative to the normal axis 32 to form an angle of reflection $\delta$ substantially equal to the angle of incidence. The optical transmitter 18 and optical receiver 20 preferably represent a conventional solid state light emitting diode transmitter and phototransitor detector combination. For a light beam divergence of less than about 12 degrees the preferred angle of incidence $\theta$ is about 55°.

The optical transmitter 18 is driven by a constant current source of power 40 through a driver circuit 42 which is intermittently interrupted at a predetermined rate by an oscillator 44. The light received by the optical receiver 20, which is a photodetector is applied as an electrical signal 45 to a peak detector circuit 46 which delivers an output signal 48 representing the average DC level of the input signal 45. A substraction circuit 50, as its name implies, provides an output signal 52 which represents the difference between a fixed DC offset reference voltage and the DC output signal 48. The fixed DC offset reference is used to initially calibrate the system as will be further elaborated upon hereafter. The output signal 52 is amplified by amplifier 54 and delivered through a buffer 56 to a multiplexer 58 which transfers the signal 52 to the analog to digital converter 60 for conversion to a digitized eight bit data signal 62. The data signal is presented to the central processing unit CPU 64 of a conventional microprocessor which is programmed to read and store the data signal 62 and to evaluate it at preestablished intervals of time, in order to determine, based upon the setting of the manual control sensitivity switch SW1, whether or not an alarm should be sounded. The microprocessor 64 is also programmed to track the signal 62 for a predetermined interval of time and to use the tracked signal as a reference signal upon which to base its determination for sounding an alarm. Although a conventional microprocessor is employed which is preferably controlled through a simple software program it should be understood the operation could be carried out by functionally equivalent circuitry such as a sample and hold circuit in combination with an adjustable timing circuit.

Figure 4:
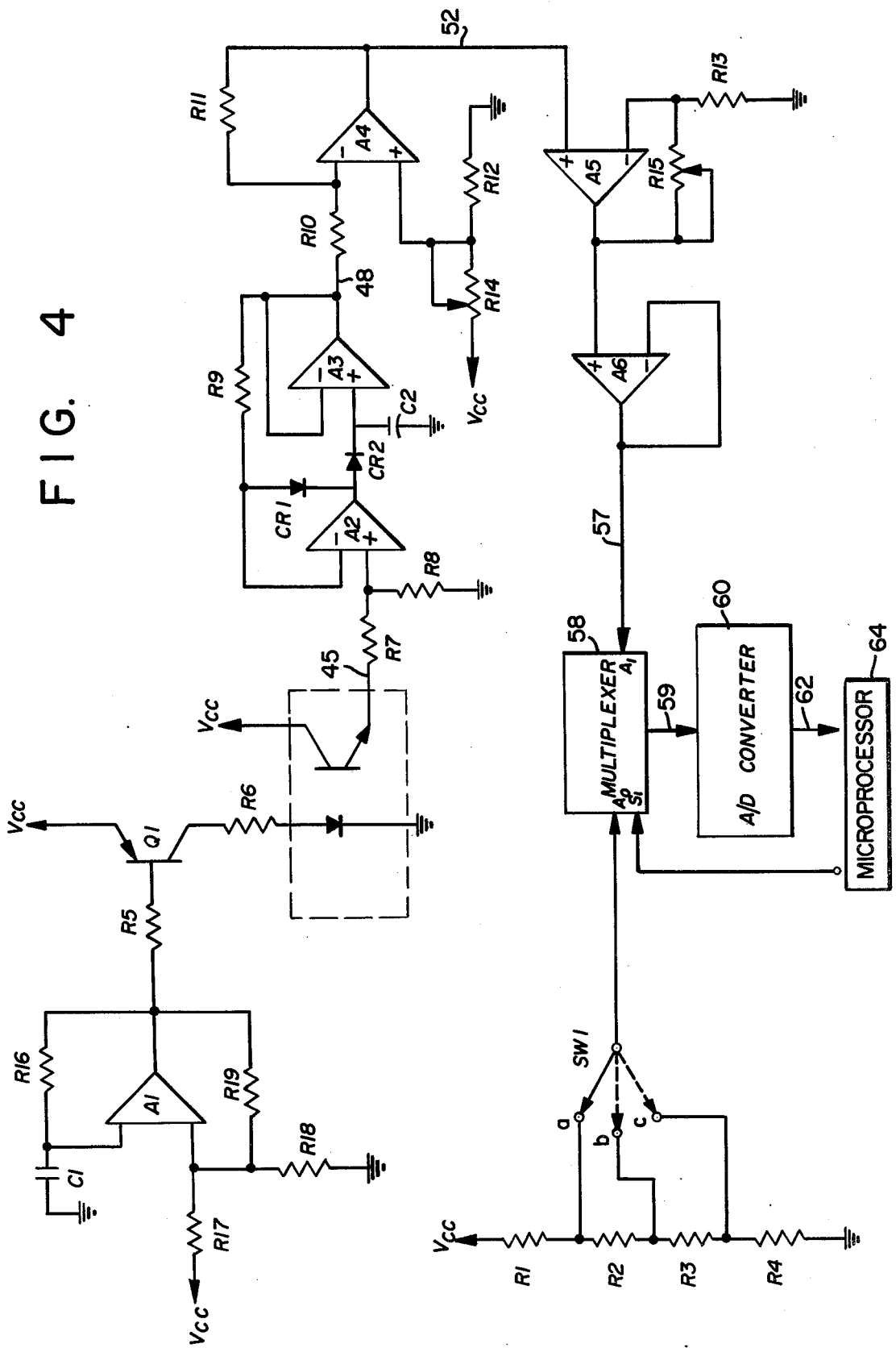
FIG. 4 is a more detailed circuit diagram of the system of FIG. 1.

A more elaborate circuit diagram of the system of FIG. 1 is shown in FIG. 4. An operational amplifier A1 is used as an astable multibrator and represents the clock oscillator 44 of FIG. 1. The frequency of oscillation is determined by the values of resistors R16, R17, R18, R19 and capacitor C1. A frequency of oscillation of less than about 100 $H_z$ is preferred. The constant current source 40 and the optical transmitter driver circuit 42 is represented by transistor Q1 in combination with resistors R5 and R6. It is important that the transistor Q1 be driven with an on time to off time ratio of approximately one. The importance of this duty cycle becomes readily apparent from the typical characteristic curve of the current transfer ratio vs. ambient temperature for an LED. The slope of the curve is steep indicating that for any small variation in ambient temperature there will be a relatively large change in the current transfer ratio which would, if permitted, cause substantial variations in the light output signal strength. It has been found that driving the light transmitter 18 intermittently with a substantially equal ratio of on time to off time will minimize changes in ambient temperature.

The output 45 of the optical receiver 20 is applied to the peak detector 46 of FIG. 1 which comprises operational amplifiers A2, A3 in combination with diodes CR1 and CR2 and a charging capacitor C2. Capacitor C2 charges to a DC level related to the average DC level of signal 45. The diode CR2 prevents discharge of capacitor Q2 through operational amplifier A2. The feedback loop of resistor R9 from the output of operational amplifier A3 to the input of operational amplifier A2 minimizes drift due to the DC input bias of operational amplifier A3. Diode CR1 compensates for leakage current flow through diode CR2.

The output 48 of the peak detector circuit 46 is applied to the subtracting circuit 50 of FIG. 1 which is shown in FIG. 4 comprising operational amplifier A4 and an offset voltage adjustment circuit including resistor R12 and variable resistor R14. Vcc is the DC bias supply source voltage for the system. The absence of blood in the dialysate solution 26 passing the optical transducer block assembly 22 will produce a threshold light energy signal which is reflected as a background DC signal at the output 48 of the peak detector 46. The system is initially calibrated by nulling out the background DC signal in the substraction circuit 52 using an equivalent offset voltage. This initial calibration is accomplished by adjustment of variable resistor R14 until the output signal 52 is zero.

The output signal 52 is applied to amplifier A5 connected as a non-inverter with an adjustable gain setting provided by variable resistor R15. The amplifier A5 is isolated by an operational amplifier A6 connected in a non-inverting fashion. The operational amplifier A6 represents the buffer 56 in FIG. 1. The output 57 from operational amplifier A6 is applied to the multiplexer 58 at port A1. The multiplexer 58 is a conventional device which is commercially available and represents a single pole multiposition electronic switch whose positions are determined by a logic level at input S1. The port A0 of the multiplexer is connected to a manually adjustable switch SW1 which has a plurality of switch positions a, b, c, representing different sensitivity levels determined by the selected combination of resistors R1, R2, R3 and R4 respectively. The output 59 of the multiplexer 58 is connected to a conventional analog to digital converter such as model No. AD571 manufactured by Analog Device Inc. The analog to digital converter provides an eight bit digital signal 62 corresponding to the analog signal 59. The digitized eight bit data signal 62 is fed to the conventional microprocesser 64.

In normal operation the microprocessor tracks the input signal 62 after the dialysis operation is started and at the end of a predetermined time stores into memory the input signal 62 as a reference calibration signal. If blood should leak through the dialyzer member 14 into the dialysate circuit 12 the light reflected by red blood cells passing the optical transducer assembly will cause the DC output signal 48 to change which will provide a corresponding change in the digital data 62 to the microprocessor 64 which in turn determines whether the change in signal output is sufficient to warrant the sounding of an alarm based upon the sensitivity level position selected by the patient.

What is claimed is:

1. A method for detecting the presence of blood in the dialysate flowstream of a hemodialysis system comprising the steps of:
    transmitting a narrow beam of light into said dialysate flowstream from one side thereof in a direction incident upon the central axis of the flowstream with a predetermined angle of incidence relative to an axis normal to said central axis;
    locating an optical receiver in a substantially common plane with said narrow beam of light and on the same side of said flowstream such that it forms an included angle of reflection with said normal axis substantially equal to said angle of incidence;
    interrupting said transmission of light at a relatively low repetition rate with the ratio of on time to off time being substantially equal;
    detecting the average DC level of the signal received by said optical receiver; and
    generating an alarm signal when said average DC level exceeds a predetermined level.

2. A method as defined in claim 1 wherein said predetermined angle of incidence is substantially about 55°.

3. A method as defined in claim 2 further comprising the steps of:
    substracting a predetermined DC offset voltage from said average DC level;
    converting the substracted signal into a digital signal;
    storing said digital signal as a digital reference signal at the end of a first predetermined time;
    repeatedly comparing said digital reference signal to said digital signal following said first predetermined time; and
    generating said alarm signal when said digital signal varies from digital reference.

4. A method as defined in claim 3 wherein said repetition rate for interrupting said transmission of light is above zero and below about 100 H$_z$.

5. A method as defined in claim 4 wherein said narrow beam of light has a beam divergence of no more than about 12°.

6. A sensor system for detecting the presence of blood in a conduit through which a dialysate solution flows for performing artificial kidney hemodialysis comprising:
    an optical transmitter connected on one side of said conduit for transmitting a narrow beam of light into said dialysate solution at a predetermined angle of incidence relative to an axis normal to said central axis;
    an optical receiver connected to said conduit on the same side thereof as said transmitter in substantially the same plane and at a predetermined angle of reflection relative to said normal axis for receiving reflected light from said dialysate solution, said angle of reflection being substantially equal to said predetermined angle of incidence;
    means for intermittently passing pulses of direct current through said optical transmitter at a relatively low frequency with a pulse width being at least substantially equal in duration to the time separation between pulses;
    means for detecting the output of said optical receiver;
    means for generating an output DC signal responsive to the average DC level of said detected output; and
    means responsive to said output DC signal for providing an output alarm signal when said output DC signal exceeds a predetermined level.

7. A system as defined in claim 6 wherein said predetermined angle of incidence is substantially about 55°.

8. A system as defined in claim 7 wherein said means for intermittently passing pulses of direct current through said optical transmitter comprises an oscillator and means for generating a constant current during a predetermined portion of each oscillating cycle.

9. A system as defined in claim 8 wherein said means for generating a DC output signal comprises a peak envelop detector.

10. A system as defined in claim 9 wherein said means for providing an output alarm signal comprises:
    a difference amplifier having one input connected to said output DC signal and a second input connected to the output of an adjustable DC reference source,
    means for converting the output of said difference amplifier into a digital control signal; and
    microcomputer means for tracking said digital control signal for a first predetermined period of time, storing said digital control signal as a digital reference signal at the end of said first period of time and comparing said digital reference signal to said digital control signal following said first predetermined period of time.

* * * * *